(12) United States Patent
    Ishikawa

(10) Patent No.: US 11,138,736 B2
(45) Date of Patent: Oct. 5, 2021

(54) INFORMATION PROCESSING APPARATUS AND INFORMATION PROCESSING METHOD

(71) Applicant: CANON KABUSHIKI KAISHA, Tokyo (JP)

(72) Inventor: Ryo Ishikawa, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 102 days.

(21) Appl. No.: 16/273,990

(22) Filed: Feb. 12, 2019

(65) Prior Publication Data
    US 2019/0251691 A1    Aug. 15, 2019

(30) Foreign Application Priority Data
    Feb. 15, 2018    (JP) ............... JP2018-025039

(51) Int. Cl.
    *G06T 7/00*       (2017.01)
    *G06T 5/40*       (2006.01)
    (Continued)

(52) U.S. Cl.
    CPC ............ *G06T 7/0016* (2013.01); *A61B 5/055* (2013.01); *A61B 5/4848* (2013.01); *A61B 5/743* (2013.01); *A61B 5/7425* (2013.01); *A61B 6/463* (2013.01); *A61B 8/463* (2013.01); *G06T 5/009* (2013.01); *G06T 5/40* (2013.01); *G06T 5/50* (2013.01); *G06T 7/168* (2017.01); *G16H 30/40* (2018.01); *A61B 2576/00* (2013.01); *G06T 11/206* (2013.01); *G06T 2207/20224* (2013.01); *G06T 2207/30096* (2013.01)

(58) Field of Classification Search
    None
    See application file for complete search history.

(56) References Cited

U.S. PATENT DOCUMENTS

2012/0033865 A1*  2/2012  Fischer ............... G06T 7/0012
                                              382/128
2013/0094734 A1*  4/2013  Rauch .................. G06T 7/38
                                              382/130
(Continued)

FOREIGN PATENT DOCUMENTS

JP     2013-126575 A    6/2013

*Primary Examiner* — Delomia L Gilliard
(74) *Attorney, Agent, or Firm* — Canon U.S.A., Inc. IP Division

(57) ABSTRACT

An information processing apparatus includes an image acquisition unit, a correspondence relation acquisition unit, an image transformation unit, a change calculation unit, and a statistics amount calculation unit. The image acquisition unit acquires a first image and a second image. The correspondence relation acquisition unit acquires a spatial correspondence relation between the first and the second images. The image transformation unit acquires a transformed image by transforming the second image to substantially coincide with the first image based on the spatial correspondence relation. The change calculation unit calculates a volume or area change between the transformed image and the second image based on the spatial correspondence relation. The statistics amount calculation unit calculates a statistics amount for pixel values of the transformed image based on the volume or area change.

10 Claims, 8 Drawing Sheets

(51) Int. Cl.
*G06T 7/168* (2017.01)
*G06T 5/00* (2006.01)
*G16H 30/40* (2018.01)
*G06T 5/50* (2006.01)
*A61B 5/00* (2006.01)
*A61B 6/00* (2006.01)
*A61B 8/00* (2006.01)
*A61B 5/055* (2006.01)
*G06T 11/20* (2006.01)

(56) References Cited

U.S. PATENT DOCUMENTS

| | | | |
|---|---|---|---|
| 2014/0079337 A1* | 3/2014 | Kondo | G06F 16/532 382/276 |
| 2016/0021335 A1* | 1/2016 | Kondo | H04N 7/0135 348/43 |
| 2019/0197687 A1* | 6/2019 | Minami et al. | |

* cited by examiner

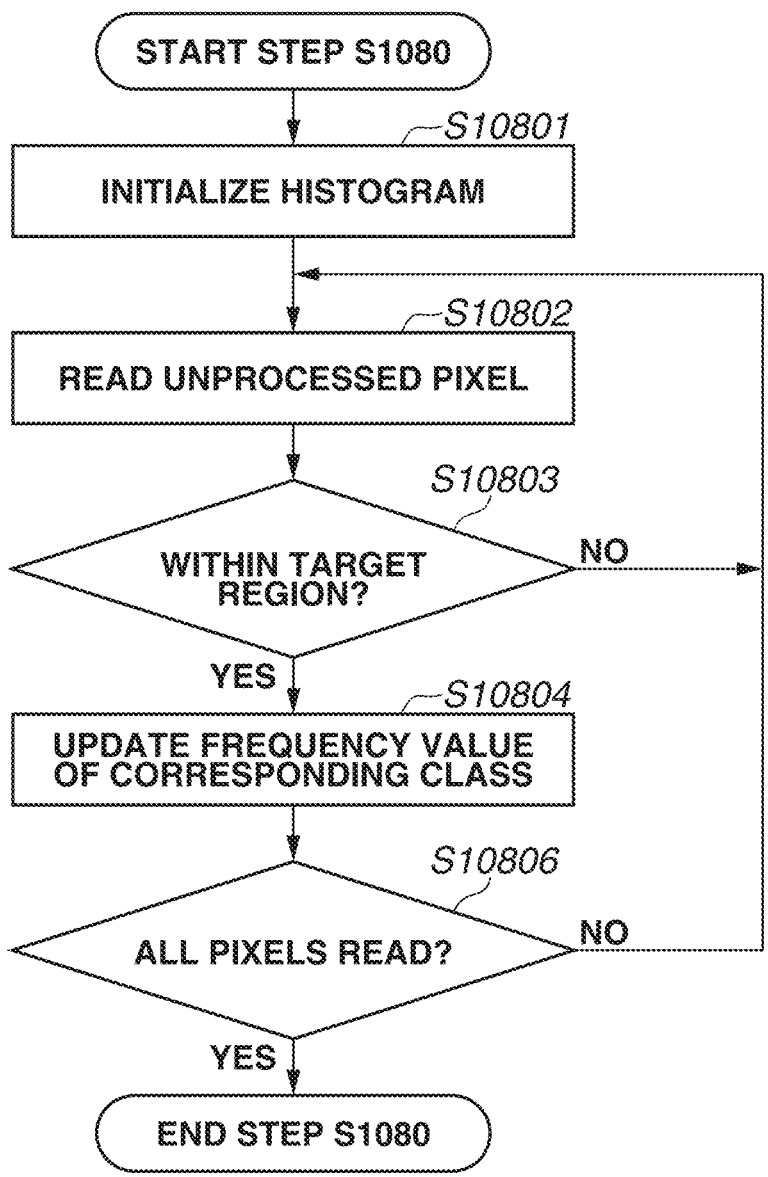

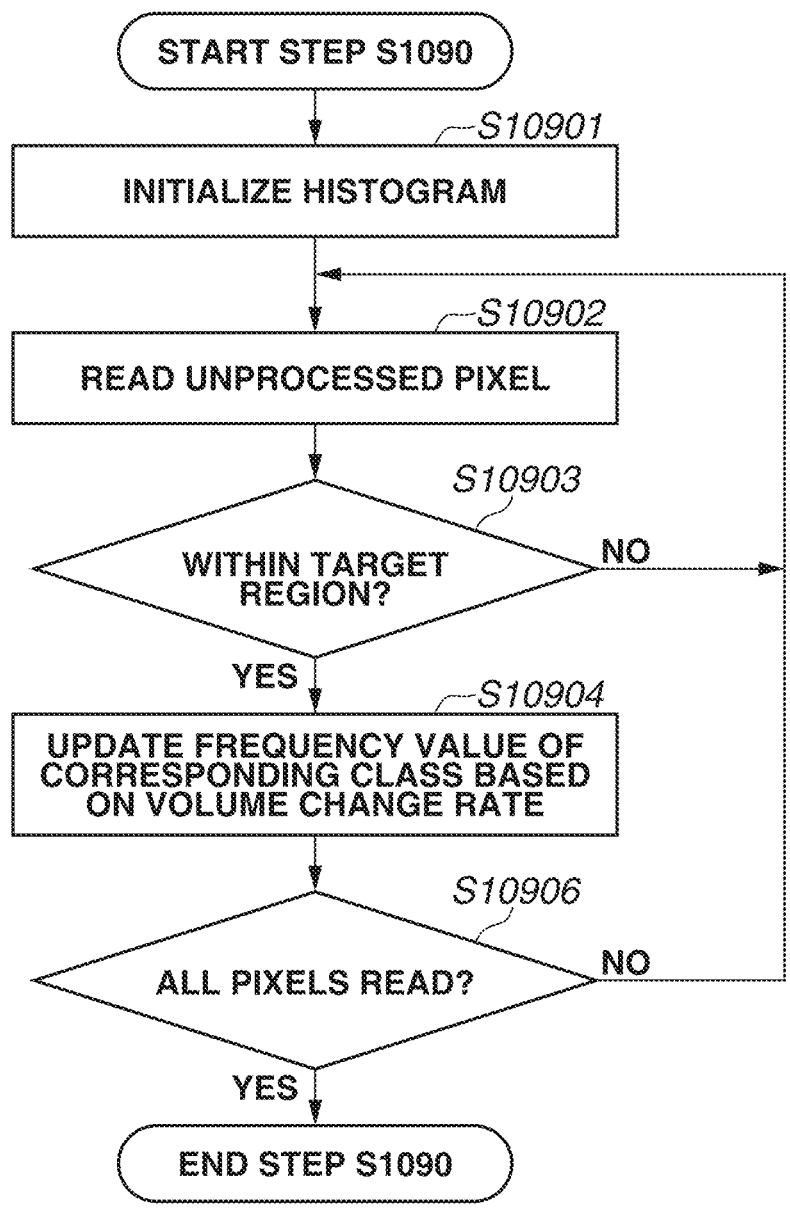

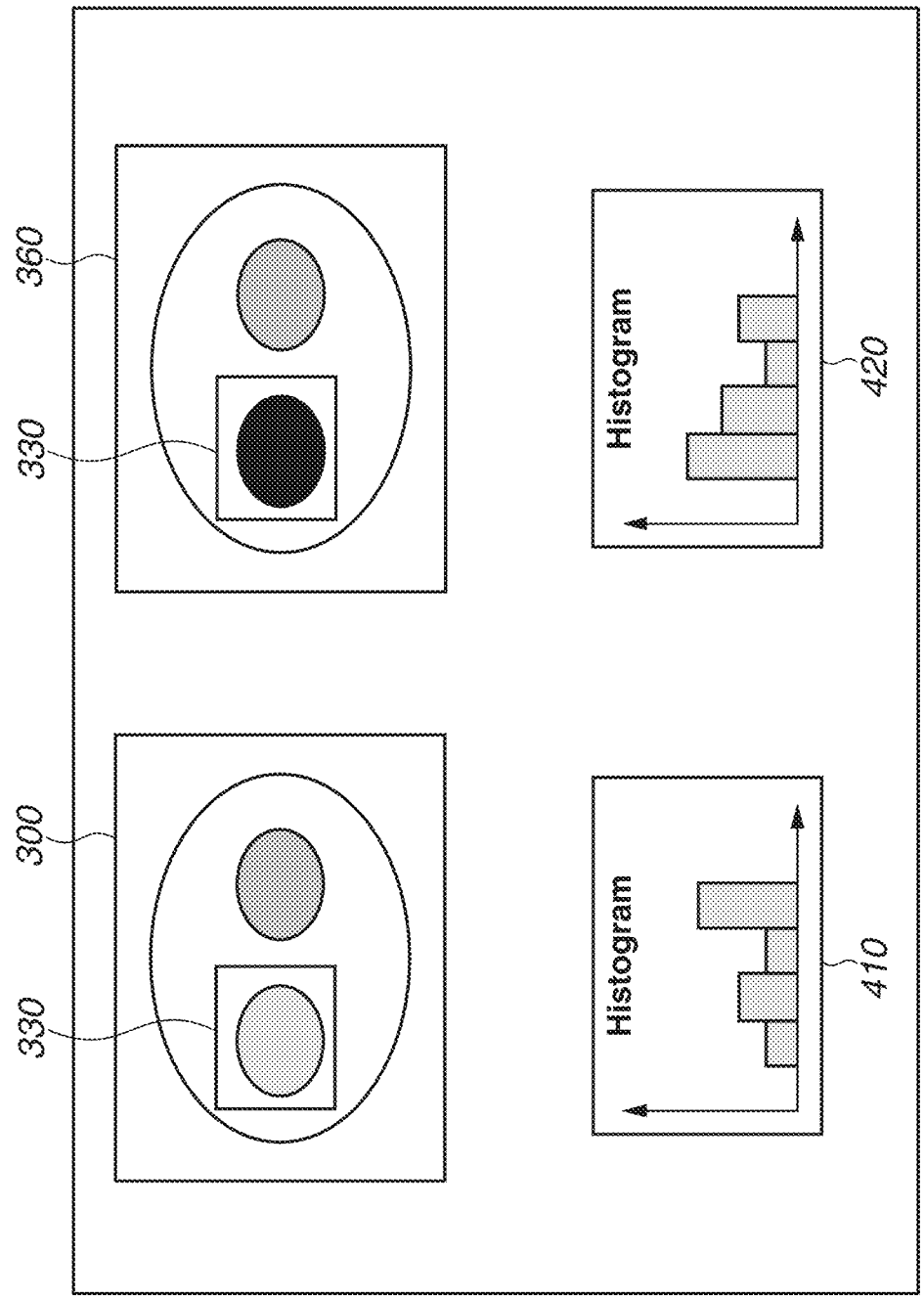

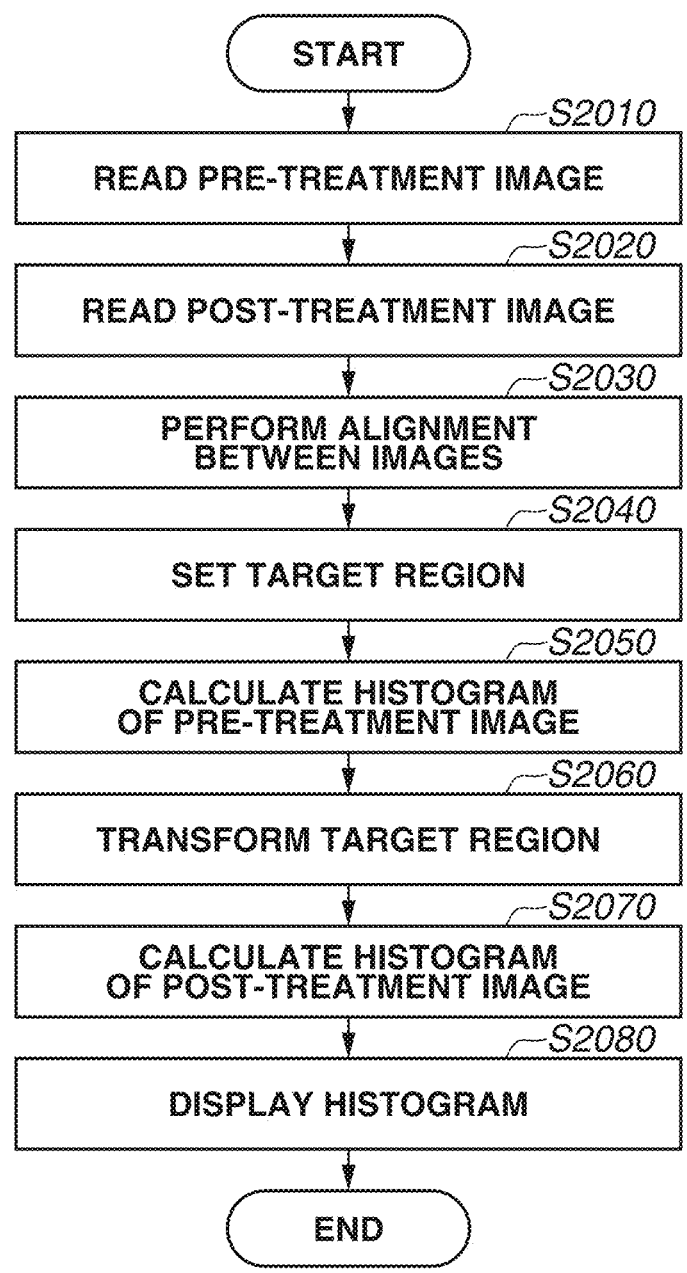

INFORMATION PROCESSING APPARATUS AND INFORMATION PROCESSING METHOD

BACKGROUND

Field

The present disclosure relates to an information processing apparatus and an information processing method.

Description of the Related Art

In the medical field, doctors perform diagnoses by using medical images captured by various modalities. In particular, in order to observe the occurrence and development of lesion, effects of medical treatments applied, and the progress of the state of a subject, a doctor contrasts a plurality of images captured at different times by using an identical modality to observe temporal changes of the subject. As a method for supporting a doctor to observe temporal changes of a subject, Japanese Patent Application Laid-Open No. 2013-126575 discusses a technique for visualizing temporal changes of lesion by providing a subtraction image generated by subtracting a comparison target image from a reference image.

However, a new technique for quantitatively measuring temporal changes has been demanded in real medical care.

SUMMARY

According to an aspect of the present disclosure, an information processing apparatus includes an image acquisition unit configured to acquire a first image and a second image, a correspondence relation acquisition unit configured to acquire a spatial correspondence relation between the first image and the second image, an image transformation unit configured to acquire a transformed image by transforming the second image to substantially coincide with the first image based on the spatial correspondence relation, a change calculation unit configured to calculate a volume or area change between the transformed image and the second image based on the spatial correspondence relation, and a statistics amount calculation unit configured to calculate a statistics amount for pixel values of the transformed image based on the volume or area change.

Further features will become apparent from the following description of exemplary embodiments with reference to the attached drawings.

BRIEF DESCRIPTION OF THE DRAWINGS

FIG. 4 is a flowchart illustrating details of processing performed in step S1080 according to the first exemplary embodiment.

FIG. 5 is a flowchart illustrating details of processing performed in step S1090 according to the first exemplary embodiment.

FIG. 6 is a diagram illustrating details of processing performed in step S1095 according to the first exemplary embodiment in detail.

FIG. 8 is a flowchart illustrating overall processing according to the second exemplary embodiment.

DESCRIPTION OF THE EMBODIMENTS

A medical information processing system according to a first exemplary embodiment provides users such as doctors and operators in medical institutions with the following functions. The medical information processing system enables a user to quantitatively measure changes in pixel values in a target region such as lesion in inspection images before radiological treatment (hereinafter referred to as a pre-treatment image) and an inspection image after radiological treatment (hereinafter referred to as a post-treatment image) relating to a target patient (subject) subjected to a medical treatment. More specifically, the medical information processing system enables a user to measure the statistics amount of pixel values in the target region in the pre-treatment image and the statistics amount of pixel values in the region in post-treatment image corresponding to the target region (hereinafter referred to as a correspondence region). The measurement of difference between the inspection images before and after radiological treatment is to be considered as illustrative, and any other images can be processed as long as the measurement is intended to make the comparison between a plurality of images.

Figure 1:
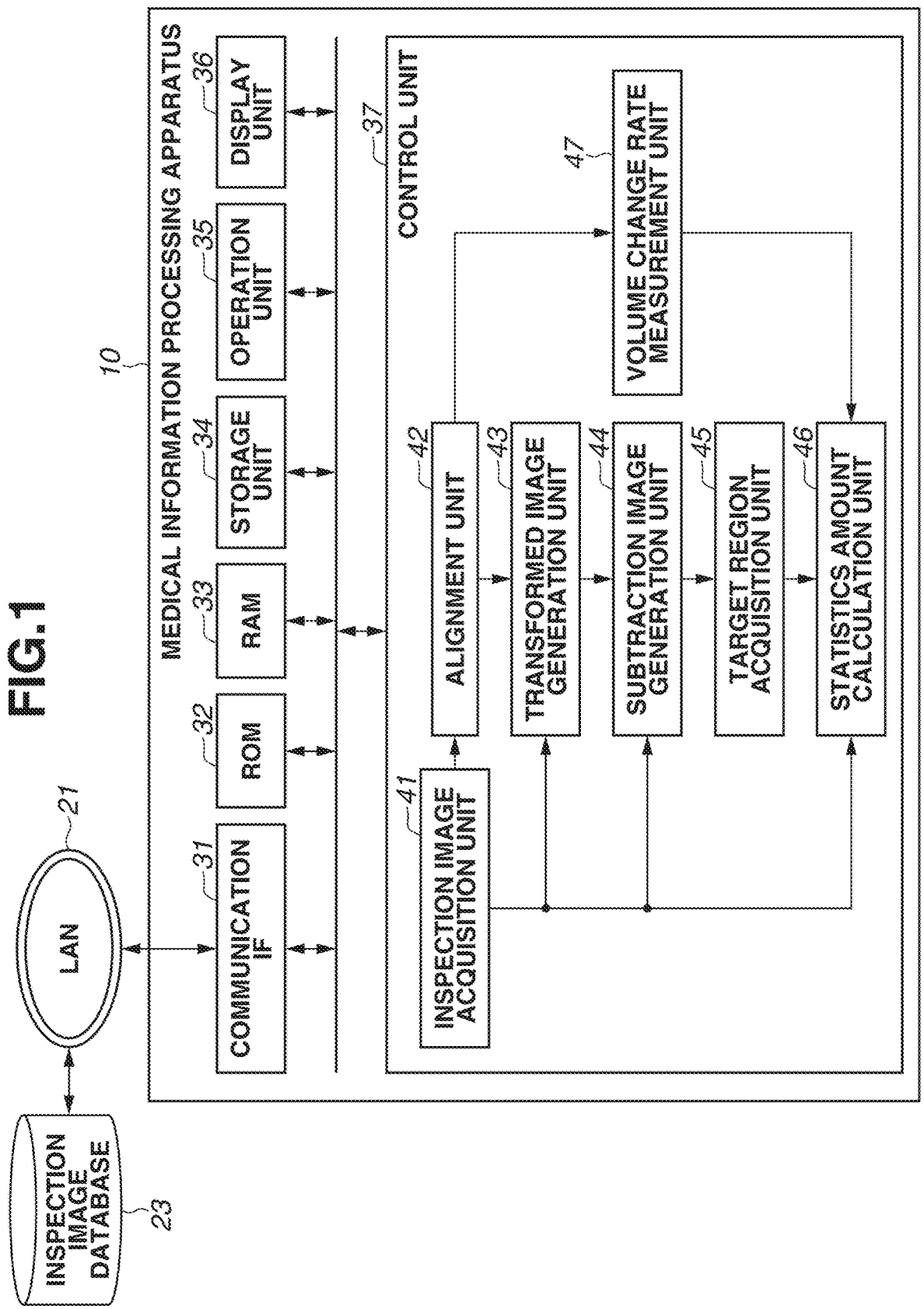
FIG. 1 is a block diagram illustrating an apparatus configuration of a medical information processing system according to a first exemplary embodiment.

FIG. 1 is a block diagram illustrating an overall configuration of the medical information processing system according to the present exemplary embodiment. The medical information processing system includes a medical information processing apparatus 10 (information processing apparatus) and an inspection image database 23 that are communicably connected with each other via a communication means. While, in the present exemplary embodiment, the communication unit is composed of a local area network (LAN) 21, it can be composed of a wide area network (WAN). The connection method of the communication means can be either wired connection or wireless connection.

The inspection image database 23 stores a plurality of inspection images relating to a plurality of patients and additional information to the inspection images. An inspection image is a medical image captured, for example, by an image diagnosis apparatus such as a computer tomography (CT) apparatus and a magnetic resonance imaging (MRI) apparatus. Inspection images include various types of images such as two- and three-dimensional images, and monochrome and color images. The additional information to an inspection image includes a name of a patient (patient identifier (ID)), inspection date information (date when the inspection image was captured), and an imaging modality name of the captured inspection image. The inspection date information can include the date and the time when the inspection image was captured. A unique number (inspection image ID) is supplied to an inspection image and additional information to enable identification from other images. The medical information processing apparatus 10 can read information based on the number. When the inspection image is a three-dimensional volume image composed of a plurality of two-dimensional tomographic images, the inspection image ID is supplied to both two-dimensional tomographic images and the three-dimensional volume image as a set of the two-dimensional tomographic images. In addition to a function of reading the above-described information, the inspection image database 23 offers a function of displaying a list of inspection images, a function of displaying thumbnails of inspection images, a function of searching for an inspection image, and a function of writing information about inspection images in cooperation with the medical information processing apparatus 10.

The medical information processing apparatus 10 acquires information stored in the inspection image database 23 via the LAN 21. The medical information processing apparatus 10 includes a communication interface (IF) 31, a read only memory (ROM) 32, a random access memory (RAM) 33, a storage unit 34, an operation unit 35, a display unit 36, and a control unit 37 as function components.

The communication IF 31 is implemented by, for example, a LAN card and manages communications between an external apparatus (e.g., an inspection image database 23) and the medical information processing apparatus 10 via the LAN 21. The ROM 32 is implemented by, for example, a nonvolatile memory and stores various programs. The RAM 33 is implemented by, for example, a volatile memory and temporarily stores various information. The storage unit 34 is implemented by, for example, a hard disk drive (HDD) and stores various information. The operation unit 35 is implemented by, for example, a keyboard and a mouse and inputs an instruction from a user to the apparatus. The display unit 36 is implemented by, for example, a display and displays various information to a user (e.g., a doctor). The operation unit 35 and the display unit 36 offer functions as graphical user interfaces (GUIs) under the control of the control unit 37.

The control unit 37 is implemented by, for example, at least one central processing unit (CPU) and integrally controls processing in the medical information processing apparatus 10. The control unit 37 includes an inspection image acquisition unit 41, an alignment unit 42, a transformed image generation unit 43, a subtraction image generation unit 44, a target region acquisition unit 45, a statistics amount calculation unit 46, and a volume change rate measurement unit 47 as function components.

The inspection image acquisition unit 41 acquires an inspection image of a patient from the inspection image database 23 via the communications IF 31 and the LAN 21 by a user operation input from the operation unit 35.

The alignment unit 42 performs alignment between a plurality of inspection images acquired by the inspection image acquisition unit 41.

Based on the result of the alignment by the alignment unit 42, the transformed image generation unit 43 transforms the inspection image acquired by the inspection image acquisition unit 41 based on the result of the alignment by the alignment unit 42.

The subtraction image generation unit 44 generates a subtraction image between the inspection image and the transformed image.

The target region acquisition unit 45 acquires a target region based on the subtraction image.

The statistics amount calculation unit 46 calculates the statistics amount of pixel values in the target region of the inspection image.

Based on the result of the alignment by the alignment unit 42, the volume change rate measurement unit 47 measures the volume change rate caused by the image transformation by the transformed image generation unit 43.

At least a part of each unit included in the control unit 37 can be implemented by an independent apparatus. In addition, each unit can be implemented by software for implementing each function. In this case, the software for implementing each function can operate on a cloud or server via a network. According to the present exemplary embodiment, each unit is assumed to be implemented by software in a local environment.

The configuration of the medical information processing system illustrated in FIG. 1 is to be considered as illustrative. For example, the storage unit 34 of the medical information processing apparatus 10 can include the function of the inspection image database 23 and store a plurality of inspection images and additional information for a plurality of patients.

Figure 2:
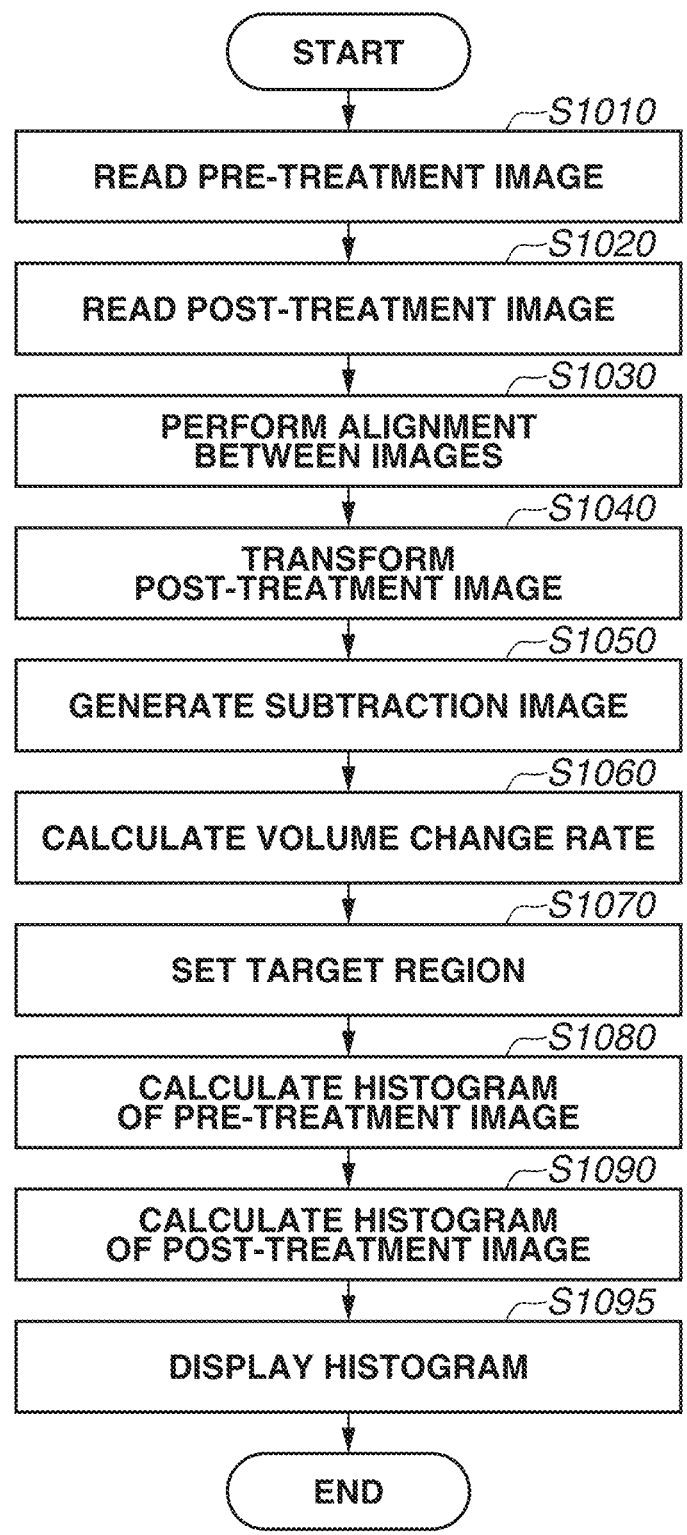
FIG. 2 is a flowchart illustrating overall processing according to the first exemplary embodiment.

Overall processing of the medical information processing apparatus 10 according to the present exemplary embodiment will be described in detail below with reference to the flowchart illustrated in FIG. 2. While the following descriptions will be made centering on an example case where CT images are used as inspection images, the implementation of the present invention is not limited thereto. MRI images and ultrasonic-wave images are also applicable.

<Reading Pre-Treatment Image>

Figure 3A:
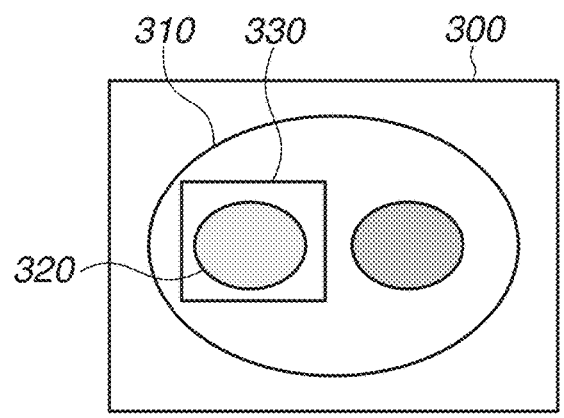
FIGS. 3A, 3B, 3C, and 3D are diagrams respectively illustrating a pre-treatment image, a post-treatment image, a transformed image, and a subtraction image, respectively, according to the first exemplary embodiment.

In step S1010, the inspection image acquisition unit 41 performs processing for acquiring a pre-treatment image to be processed from the inspection image database 23. In other words, this processing is equivalent to an example of an image acquisition method for acquiring a first image and a second image. A pre-treatment image according to the present exemplary embodiment is a three-dimensional CT image and is a set of pixels arranged at equal intervals in each direction of three-dimensional coordinate axes. According to the present exemplary embodiment, a pre-treatment image is referred to as a pre-treatment image I1 or a function I1(x) that has an argument of the coordinate value x of a pre-treatment image in the image coordinate system and returns pixel values of the pre-treatment image I1. When the coordinate value x given as an argument indicates a position between pixels, the function I1(x) interpolates pixel values of surrounding pixels and returns pixel values of the position. Applicable interpolation methods include a generally known linear interpolation and any other known methods. FIG. 3A illustrates a pre-treatment image 300 or the pre-treatment image I1 according to the present exemplary embodiment. While the pre-treatment image I1 is a three-dimensional image, the pre-treatment image I1 is replaced with a two-dimensional cross-sectional image for the convenience of descriptions. The pre-treatment image 300 includes a subject 310 and a pre-treatment affected region 320 inside the subject 310.

<Reading Post-Treatment Image>

Figure 3B:
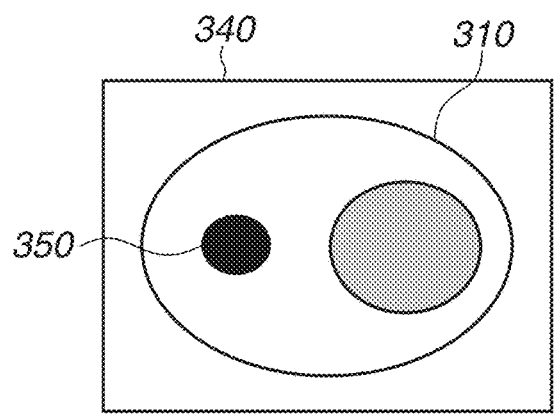

In step S1020, the inspection image acquisition unit 41 performs processing for acquiring a post-treatment image to be processed from the inspection image database 23. In other words, this processing is equivalent to an example of an image acquisition method for acquiring a first image and a second image. Specific processing is similar to the processing in step S1010 and descriptions thereof will be omitted. According to the present exemplary embodiment, a post-treatment image is referred to as a post-treatment image I2 or a function I2(x). FIG. 3B illustrates a post-treatment image 340 or the post-treatment image I2 according to the present exemplary embodiment. The post-treatment image 340 includes the subject 310 like the pre-treatment image 300. The post-treatment image 340 also includes a post-treatment affected region 350 (same affected region as the pre-treatment affected region 320). The present exemplary embodiment will be described below centering on an example case where the post-treatment affected region 350 is smaller in size than the pre-treatment affected region 320.

<Alignment Between Images>

In step S1030, the alignment unit 42 performs alignment between the pre-treatment image I1 and the post-treatment image I2. The present exemplary embodiment will be described below centering on an example case where transformed alignment is performed as alignment between the pre-treatment image I1 and the post-treatment image I2. Alignment processing refers to processing for obtaining a positional correspondence relation between images, i.e., processing for estimating a transformation between images. Alignment between images can be performed by using any of known methods. For example, the positional correspondence relation between images is obtained by transforming one image to increase the image similarity between images after the transformation. Applicable methods for increasing the image similarity include Sum of Squared Difference (SSD) generally used, the mutual information amount, the cross correlation coefficient, and other known methods. Applicable models of image transformation include a transformed model based on a radial basis function such as Thin Plate Spline (TPS) and include known transformed models such as Free Form Transformation (FFD) and Large Transformation Diffeomorphic Metric Mapping (LDDMM). With the above-described method, processing for position-aligning the post-treatment image to the pre-treatment image is performed, and the correspondence relation between the image coordinates of the post-treatment image and the image coordinates of the pre-treatment image is calculated. According to the present exemplary embodiment, the correspondence relation is acquired as a transform function D(x). In other words, this processing is equivalent to an example of a correspondence relation acquisition method for acquiring a spatial correspondence relation between the first and the second images. The transform function D(x) is a function that returns the image coordinate value (three-dimensional vector) of the position corresponding to the post-treatment image using an argument of the image coordinate value (three-dimensional vector) of the pre-treatment image.

<Transforming Post-Treatment Image>

In step S1040, the transformed image generation unit 43 performs processing for generating a transformed image (transformed image) by transforming the post-treatment image I2 so as to substantially coincide with the pre-treatment image I1, based on the transform function D(x) acquired in the processing in step S1030. In other words, this processing is equivalent to an example of an image transformation method for acquiring a transformed image by transforming the second image so as to substantially coincide with the first image based on the correspondence relation. More specifically, pixel values at each position x of a transformed image I3(x) are calculated through the calculation represented by the formula (1).

$$I3(x)=I2\{D(x)\} \quad (1)$$

Image transformation based on a transform function can be performed by using any of known methods. According to the present exemplary embodiment, a transformed image generated in the above-described processing is referred to as a transformed image I3 or a function I3(x).

Figure 3C:
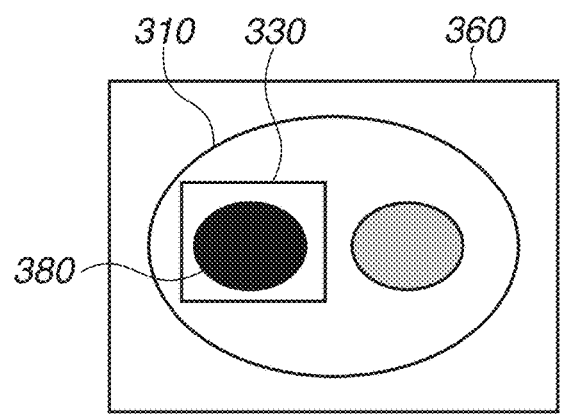

FIG. 3C illustrates a transformed image 360 generated in step S1040. The transformed image 360 is generated by transforming the post-treatment image 340 so that the shape of each region and the pixel value distribution of the post-treatment image 340 substantially coincide with those of the pre-treatment image 300. Accordingly, a post-treatment affected region 380 included in the transformed image 360 is larger in size than the post-treatment affected region 350 drawn in the post-treatment image 340 and is similar in size to the pre-treatment affected region 320 included in the pre-treatment image 300. In this way, the processing in step S1030 performs alignment for the change in size between the pre-treatment affected region 320 and the post-treatment affected region 350. The change in size is absorbed by the transformed image 360 since the transformed image 360 is generated based on the alignment result.

<Generating Subtraction Image>

Figure 3D:
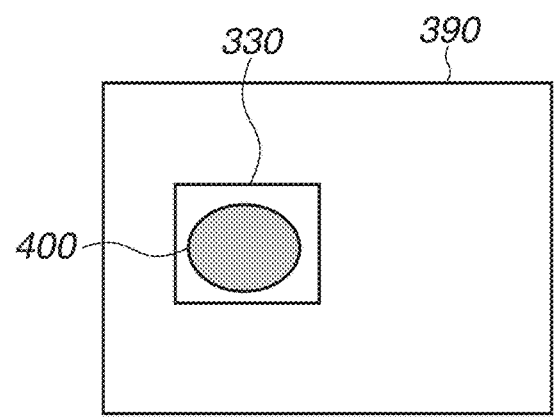

In step S1050, the subtraction image generation unit 44 performs processing for generating a subtraction image between the pre-treatment image I1 and the transformed image I3. In other words, this processing is equivalent to an example of a subtraction image generation method for generating a subtraction image between the first image and the transformed image. FIG. 3D illustrates a subtraction image 390 generated in step S1050. The subtraction image 390 draws differences between the pre-treatment affected region 320 and the post-treatment affected region 400 in the transformed image 360. In this case, the change in size of an affected region is absorbed through alignment, and only differences in pixel values of the affected region are obtained. According to the present exemplary embodiment, a subtraction image generated in step S1050 is referred to as a subtraction image I4 or a function I4(x). The generation of the subtraction image I4 can be performed by using any of known methods. For example, the subtraction image I4 can be generated through a simple subtraction operation represented by the formula (2).

$$I4(x)=I3(x)-I1(x) \quad (2)$$

The generated substance of the subtraction image I4 can be stored by using memory functions such as the ROM 32, the RAM 33, and the storage unit 34 included in the medical information processing apparatus 10. When the subtraction image I4 is referenced in processing described below, the value of the subtraction image I4 at the referenced position can be acquired through the calculation by the formula (2). The method for calculating the subtraction image I4 is not limited to the above-described simple example based on the formula (2). For example, a subtraction image can be generated in consideration of the distribution of pixel values of the tissue of the target region and surrounding tissues. For example, when the target region subjected to radiological treatment is a bone, pixel values of the bone in a CT image are higher than pixel values of other regions. Accordingly, the subtraction image I4 can be generated by emphasizing difference values in high pixel values and reducing difference values in other pixel values. This processing has an effect of generating a subtraction image which makes it easier to visually recognize a change in the target region out of changes in the subject occurring before and after the treatment. The method for generating a subtraction image is not limited thereto. A subtraction image can be generated by removing various kinds of noise irrelevant to the difference before and after the treatment. The processing can proceed to step S1060 without generating a subtraction image. A subtraction image needs to be generated in step S1050 when a target region is set based on a subtraction image, like a modification 1-1 described below. Therefore, it is not always necessary to perform processing in step S1050.

<Calculating Volume Change Rate>

In step S1060, the volume change rate measurement unit 47 performs processing for calculating the volume change rate by the transformation from the transformed image I3 into the post-treatment image I2 based on the transform function D(x) acquired in step S1030. In other words, this processing is equivalent to an example of a change calculation method for calculating the volume or area change between the transformed image and the second image based on the correspondence relation. When the first and the second images are three-dimensional images, this processing is also equivalent to an example of a change calculation method characterized in calculating the volume change between the transformed image and the second image based on the correspondence relation. More specifically, the volume change rate measurement unit 47 calculates a 3 by 3 Jacobian-matrix J(x) as a spatial differentiation on the transform function D(x) calculated in step S1030, through the calculation represented by the formula (3).

$$J(x) = \frac{\partial D(x)}{\partial x} = \begin{pmatrix} \frac{\partial D_x(x)}{\partial x} & \frac{\partial D_x(x)}{\partial y} & \frac{\partial D_x(x)}{\partial z} \\ \frac{\partial D_y(x)}{\partial x} & \frac{\partial D_y(x)}{\partial y} & \frac{\partial D_y(x)}{\partial z} \\ \frac{\partial D_z(x)}{\partial x} & \frac{\partial D_z(x)}{\partial y} & \frac{\partial D_z(x)}{\partial z} \end{pmatrix} \quad (3)$$

Dx(x), Dy(x), and Dz(z) indicate component values of the transform function D(x) in the three axial directions of the value (three-dimensional vector) at a position x=(x, y, z). If the transform function D(x) is an identify function (function that returns the value of the argument as it is), the Jacobian matrix J(x) becomes a 3 by 3 unit matrix.

As represented by the formula (4), the volume change rate measurement unit 47 calculates a volume change rate Vc(x) by calculating the determinant of the Jacobian matrix J(x).

$$Vc(x)=|J(x)| \quad (4)$$

The volume change rate Vc(x) is a scalar function transformed image that returns the local volume change rate accompanying the coordinate transformation from the coordinate value of the transformed image I3 into the coordinate value of the post-treatment image I2 at the position using an argument of the coordinate value x of the transformed image I3. A Vc(x) value of 1.0 indicates that a local volume change rate has not occurred at the position x. A Vc(x) value of 0.5 means that, when the local region at the position of the transformed image I3 is projected on the coordinate system of the post-treatment image I2, the volume is reduced (compressed) to 0.5 times, i.e., the volume becomes half. A Vc(x) value of 2.0 means that, when the local region at the position of the transformed image I3 is projected on the coordinate system of the post-treatment image I2, the volume is increased (expanded) to 2.0 times.

<Setting Target Region>

In step S1070, the target region acquisition unit 45 performs processing for acquiring the target region of the subject. In other words, this processing is equivalent to an example of a target region acquisition method for acquiring the target region in the first image. The target region according to the present exemplary embodiment is defined as a target region 330 in the pre-treatment image 300, as illustrated in FIG. 3A. The target region 330 is defined as a region including the affected region 320 included in the pre-treatment image 300. For example, the pre-treatment image 300 is displayed on the display unit 36 for visual recognition by the user. The user can set the target region 330 on the pre-treatment image 300 via the operation unit 35. Similarly, the transformed image 360 and the subtraction image 390 aligned with the pre-treatment image 300 can be displayed on the display unit 36 to enable the user to set a target region on these images. A target region may be a three-dimensional region or a two-dimensional region.

According to the present exemplary embodiment, the target region acquired in the above-described processing is referred to as R or a function R(x). The function R(x) is a binary function that returns whether an arbitrary position x of the pre-treatment image I1 in the image coordinate system is a target region. More specifically, the function R(x)=1 when the position indicated by the coordinate value x is a target region and the function R(x)=0 otherwise. The target region R can be represented by a label image indicating a target region.

<Calculating Histogram of Pre-Treatment Image>

In step S1080, the statistics amount calculation unit 46 performs processing for calculating the statistics amount for pixel values of the target region R in the pre-treatment image I1. The present exemplary embodiment will be described below centering on a method for calculating a volume histogram H1 relating to the frequency of pixel values (of the target region R of pre-treatment image I1) as a specific example of the statistics amount for pixel values. The procedure of this processing will be described in detail below with reference to FIG. 4.

<Initializing Histogram>

In step S10801, the statistics amount calculation unit 46 initializes the histogram H1 (including bins H1_i (1≤i≤N)), where the subscript i denotes the index of bins of the histogram and N denotes the number of classes of the histogram. In this case, the statistics amount calculation unit 46 initializes the histogram H1 having N bins. More specifically, the statistics amount calculation unit 46 sets the values of the bins H1_i (1≤i≤N) to 0. In this case, it is desirable to suitably set the range of pixel values corresponding to each class based on the general distribution of pixel values of the human body in a CT image.

The statistics amount calculation unit 46 repetitively performs processing from step S10802 to step S10806 until the processing ends through the determination processing in step S10806.

<Reading Unprocessed Pixel>

In step S10802, the statistics amount calculation unit 46 selects a pixel which has not yet been processed in the repetition processing from step S10802 to step S10806 out of a plurality of pixels constituting the pre-treatment image I1(x) and reads the pixel value of the pixel. This processing is performed, for example, by processing for reading pixels constituting the pre-treatment image I1(x) in order of raster scan. In the subsequent descriptions, the coordinate value of a pixel read in step S10802 is referred to as x' and the pixel value of the pixel is referred to as v'.

<Determining Whether Pixel is Within Target Region>

In step S10803, the statistics amount calculation unit 46 determines whether the coordinate value x' of the pixel selected in step S10802 is included in the target region. More specifically, when the value of the function R(x') is 1 (YES in step S10803), the processing proceeds to step S10804. When the value of the function R(x') is not 1 (NO in step S10803), the processing returns to step S10802.

<Updating Frequency Value of Applicable Class>

In step S10804, the statistics amount calculation unit 46 identifies the class into which the pixel value v' falls and performs processing for updating the histogram of the class. In other words, this processing is equivalent to an example of a statistics amount calculation method characterized in calculating the first statistics amount for pixel values of the first image. More specifically, the statistics amount calculation unit 46 performs processing for increasing the histogram of the class corresponding to the pixel value v' by the volume of the pixel. More specifically, the statistics amount calculation unit 46 performs calculation processing represented by the formula (5).

$$H1_{i'} \leftarrow H1_{i'} + d1 \qquad (5)$$

i' denotes the index of the class corresponding to the pixel value v'. d1 denotes the volume of one pixel of the pre-treatment image as a three-dimensional image. The volume of one pixel is calculated by the product of the pitch of each pixel for each coordinate axis. Since all pixels of a general three-dimensional image have the same volume, the volume d1 of one pixel can be pre-calculated before performing processing in step S1080. Therefore, in step S1080, the statistics amount calculation unit 46 can read and use the pre-calculated volume d1.

<Determining Whether all Pixels have been Read>

In step S10806, the statistics amount calculation unit 46 determines whether all pixels of the pre-treatment image I1(x) have been read in the processing in step S10802. When all pixels have been read (YES in step S10806), the processing ends the processing in step S1080. When all pixels have not been read (NO in step S10806), the processing returns to step S10802.

This completes the processing in step S1080. In this step, the statistics amount for pixel values of the target region R in the pre-treatment image I1 (volume histogram H1 relating to the frequency of pixel values as a specific example) has been calculated.

<Calculating Histogram of Post-Treatment Image>

In step S1090, the statistics amount calculation unit 46 performs processing for calculating the statistics amount of pixel values of the target region R in the transformed image I3. The present exemplary embodiment will be described below centering on a method for calculating the volume histogram H2 relating to the frequency of pixel values (of the target region R in the transformed image I3) as a specific example of the statistics amount for pixel values like step S1080. The procedure of this processing will be described in detail below with reference to FIG. 5. Processing in steps S10901 to S10903 and S10906 in step S1090 is similar to the processing in steps S10801 to S10803 and S10806 in step S1080, respectively, except that the processing target is the transformed image I3, and descriptions thereof will be omitted.

<Updating Frequency Value of Corresponding Class Based on Volume Change Rate>

In step S10904, the statistics amount calculation unit 46 identifies the class corresponding to the pixel value v' and performs processing for updating the histogram of the class. More specifically, the statistics amount calculation unit 46 performs processing for increasing the histogram of the class corresponding to the pixel value v' by the volume of the region in the post-treatment image I2 corresponding to the pixel of the transformed image I3. More specifically, the statistics amount calculation unit 46 performs calculation processing represented by the formula (6).

$$H2_{i'} \leftarrow H2_{i'} + d3 \cdot Vc(x') \qquad (6)$$

i' denotes the index of the class corresponding to the pixel value v', and d3 denotes the volume of one pixel of the transformed image as a three-dimensional image. Vc(x') denotes the volume change rate at the position of the pixel obtained in step S1060. In this way, the volume of the region in the post-treatment image I2 corresponding to the pixel is calculated by multiplying the volume (d3) of one pixel in the transformed image I3 by the volume change rate (Vc(x')) when the pixel is inverse-transformed into the post-treatment image I2 before the transformation. In other words, this processing is equivalent to an example of a statistics amount calculation method for calculating the statistics amount for pixel values of the transformed image based on the volume or area change. This processing is also equivalent to an example of a statistics amount calculation method characterized in calculating the statistics amount for pixel values of the transformed image corresponding to the target region based on the volume or area change. This processing is also equivalent to an example of a statistics amount calculation method characterized in calculating the statistics amount by correcting information about pixel values of the transformed image according to the volume or area change.

This completes the processing in step S1090. This processing makes it possible to derive the statistics amount of pixel values of the target region R in the transformed image I3 after correcting the difference in volume from the post-treatment image I2. This processing calculates the statistics amount for pixel values of the region in the post-treatment image I2 corresponding to the target region R (hereinafter referred to as a correspondence region R').

<Displaying Histogram>

In step S1095, the control unit 37 displays the statistics amount of pixel values of the target region R in the pre-treatment image I1 and the statistics amount of pixel values of the correspondence region R' in the post-treatment image I2 (e.g., the histograms H1 and H2) calculated in steps S1080 and S1090, respectively, on the display unit 36. An example of this processing will be described below with reference to FIG. 6. FIG. 6 illustrates an example of a screen configuration in display processing in step S1095. As illustrated in FIG. 6, in the processing performed in step S1095, the pre-treatment image 300 and the transformed image 360 are displayed in an arranged manner (side by side in this case), and histograms 410 and 420 calculated in steps S1080 and S1090 can be displayed in association with the pre-treatment image 300 and the transformed image 360, respectively. In this case, the post-treatment image I2 can be displayed instead of the transformed image I3. In other words, this processing is equivalent to an example of a display control method for displaying the transformed image or the second image and the statistics amount on the display unit 36 in an arranged manner (up and down in this case). This processing is also equivalent to an example of a display control method characterized in displaying the transformed image or the second image and the second statistics amount on the display unit 36 in an arranged manner and displaying the first image and the first statistics amount on the display unit 36 in an arranged manner. In this case, it is desirable to display the histogram of pixel values to enable the user to easily visually recognize which region in each image corresponds thereto, for example, by superimposing the target region 330 on each image. In addition, the change amount of the statistics amount of pixel values between the target region R in the pre-treatment image I1 and the correspondence region R' in the post-treatment image I2 (more specifically, the difference and ratio between the histograms H1 and H2) can be calculated and displayed. However, the processing for displaying the calculated statistics amount is not always necessary. Only processing for storing the calculated statistics amount in the storage unit 34 or the inspection image database 23 in association with each inspection image can be performed.

The processing by the medical information processing apparatus 10 according to the present exemplary embodiment is performed through the above-described method. This method has an effect enabling the quantitative measurement of the statistics amount of pixel values in the target region in the pre-treatment image and the region in the post-treatment image corresponding to the target region (i.e., correspondence region). In particular, it is possible to set a measurement range after identifying the correspondence region between images based on alignment between the above-described images, and eliminate the influence of a local volume change occurring in the transformed image during measurement. This method provides an effect of achieving measurement with higher accuracy.

When there is a plurality of post-treatment images, processing similar to the above-described processing can be performed on each post-treatment image to calculate and display the statistics amount of pixel values in the correspondence region R'. In a case where the statistics amount of pixel values in the target region in the pre-treatment image has been calculated by another method, only the statistics amount of pixel values in the correspondence region in the post-treatment image can be obtained. In this case, the processing in step S1080 can be omitted.

Modification Example 1-1: Method for Setting Target Region

While the first exemplary embodiment has been described above centering on an example case where the target region acquisition unit 45 receives a user operation and a target region is set based on the user operation in step S1070, the implementation of the present invention is not limited thereto. For example, a target region can be set by performing image processing on the pre-treatment image I1, the post-treatment image I2, the transformed image I3, and the subtraction image I4. For example, a treatment target internal organ can be extracted from the pre-treatment image I1, and a target region can be set in the extracted region. For example, a region automatically extracted can be set as a target region as it is, and a region having a predetermined shape (e.g., a rectangular or spherical region) including the region automatically extracted can be set as a target region. In addition, a region having large difference values in pixel values can be extracted from the subtraction image I4, and a target region can be set in the extracted region. In other words, this processing is equivalent to an example of a target region acquisition method characterized in acquiring a target region based on a subtraction image. A target region can also be set based on the interrelation between pixel values of the plurality of images. The above-described methods provide an effect of omitting or simplifying user operations for the setting of a target region and an effect of improving the quantitative performance and reproducibility for the statistics amount to be calculated. A target region does not necessarily need to be a partial region in the pre-treatment image I1. The entire range of the pre-treatment image I1 can be set as a target region.

Modification Example 1-2: Statistic of Pixel Values

While the first exemplary embodiment has been described above centering on an example case where a histogram is calculated as an example of the statistics amount of pixel values calculated by the statistics amount calculation unit 46, the implementation of the present disclosure is not limited thereto. The statistics amount of any other pixel values can also be calculated by the statistics amount calculation unit 46. For example, the statistics amount calculation unit 46 can calculate the average value of pixel values in the target region. In this case, in step S1080, the statistics amount calculation unit 46 performs the addition of pixel values and counts the number of pixels of the pre-treatment image I1 in the target region R. Then, after the processing is completed for all pixels, the statistics amount calculation unit 46 divides the addition value by the number of pixels to calculate the average value of pixel values in the target region R in the pre-treatment image I1. In step S1090, the statistics amount calculation unit 46 performs the addition of the product of the pixel value and the volume change rate at the position and counts the number of pixels of the transformed image I3 in the target region R. Then, after the processing is completed for all pixels, the statistics amount calculation unit 46 divides the addition value by the number of pixels to calculate the average value of pixel values in the correspondence region R' in the post-treatment image I2. In step S1090, the following processing can be performed other than the above-described processing. First, the statistics amount calculation unit 46 calculates an image I5(x) by multiplying the pixel value of each pixel in the transformed image I3 by the value in a volume change rate map Vc(x) having the same coordinate value as the pixel. Then, the statistics amount calculation unit 46 performs processing similar to the processing performed in step S1080 on the image I5 to calculate the average value of pixel values. Any one of the above-described methods enables calculating the average pixel value in the post-treatment image before the transformation in consideration of the volume change rate by the transformation between the transformed image and the post-treatment image.

Modification Example 1-3: Example Case of Two-Dimensional Images

While the first exemplary embodiment has been described above centering on an example case where the pre-treatment image I1 and the post-treatment image I2 are three-dimensional images, the implementation of the present disclosure is not limited thereto. For example, the pre-treatment image I1 and the post-treatment image I2 can be two-dimensional images such as plain X-ray images and fundus images. In this case, in step S1030, the statistics amount calculation unit 46 performs alignment between two-dimensional images. In step S1060, the statistics amount calculation unit 46 performs processing for calculating the local area change rate accompanying the image transformation, based on the result of the above-described alignment between the two-dimensional images. In other words, this processing is equivalent to an example of a change calculation method characterized in calculating an area change between the transformed image and the second image based on the correspondence relation when the first and the second images are two-dimensional images. In step S1070 and the subsequent steps, processing similar to the processing according to the above-described exemplary embodiment can be performed on two-dimensional images. In other words, the present disclosure is also applicable to two-dimensional images.

Modification Example 1-4: Changing Presence or Absence of Correction by Volume Change Rate While the first exemplary embodiment has been described above centering on an example case where the volume change rate accompanying the transformation between the transformed image and the post-treatment image is calculated and the statistics amount of pixel values is corrected based on the calculated volume change rate, the implementation of the present disclosure is not limited thereto. For example, the presence or absence of the correction by the volume change rate can be switched based on an arbitrary condition such as a user setting. When the correction by the volume change rate is not to be performed, then in step S1090, the statistics amount calculation unit 46 performs processing similar to the processing performed in step S1080 on the transformed image I3. For example, when it is clear that the local volume change as a result of alignment between the pre-treatment image and the post-treatment image is very small or when the influence of the volume change on the statistics amount is permissibly small, the correction by the volume change rate can be omitted to improve the processing efficiency. In addition, the condition for changing the presence or absence of the correction by the volume change rate is not limited to a case where the presence or absence of the correction is based on the user setting. For example, the statistics amount calculation unit 46 performs the processing in step S1070 before the processing in step S1060 to acquire a target region and then calculates the volume change rate in the target region. Then, based on the range of the volume change rate, distribution, and average calculated, the statistics amount calculation unit 46 can change the presence or absence of the correction by the volume change rate over the entire image range. In this case, except when the volume change rate in the target region is expected to largely affect the statistics amount calculation, the correction by the volume change rate can be omitted. When the correction by the volume change rate is performed through the above-described change, to perform the correction can be presented to the user. This processing enables the user to indirectly observe information about the volume change in the target region. In addition, both the statistics amount when the correction by the volume change rate is performed and the statistics amount when the correction is not performed can be displayed.

Modification Example 1-5: Calculating Volume Change Rate

According to the first exemplary embodiment, the statistics amount calculation unit 46 calculates, in step S1060, the volume change rate between the transformed image I3 and the post-treatment image I2 by using a Jacobian matrix as a spatial differentiation of the transform function D(x). However, the method for calculating the volume change rate is not limited thereto. The volume change rate can be calculated by using any other methods. For example, focusing on a plurality of adjacent pixels (e.g., 6-neighboring pixels having coordinates x*) of the target pixel in the transformed image I3, the statistics amount calculation unit 46 obtains the volume of a polyhedron having these adjacent pixels as vertexes and the volume of a polyhedron having the correspondence positions D(x*) with respect to the coordinates x* in the post-treatment image I2 as vertexes. Then, the statistics amount calculation unit 46 can calculate the volume change rate of the target pixel based on the ratio between the two volumes.

A second exemplary embodiment will be described below. While the first exemplary embodiment has been described above centering on an example case where the statistics amount of pixel values of the correspondence region in the post-treatment image by correcting the statistics amount of pixel values of the target region in the transformed image (as a result of transforming the post-treatment image so as to substantially coincide with the pre-treatment image) based on the volume change rate, the implementation of the present disclosure is not limited thereto. The second exemplary embodiment will be described below centering an example case where the statistics amount of pixel values of the correspondence region in the post-treatment image is calculated by performing the coordinate transformation on the target region defined on the pre-treatment image into the image coordinates of the post-treatment image.

Figure 7:
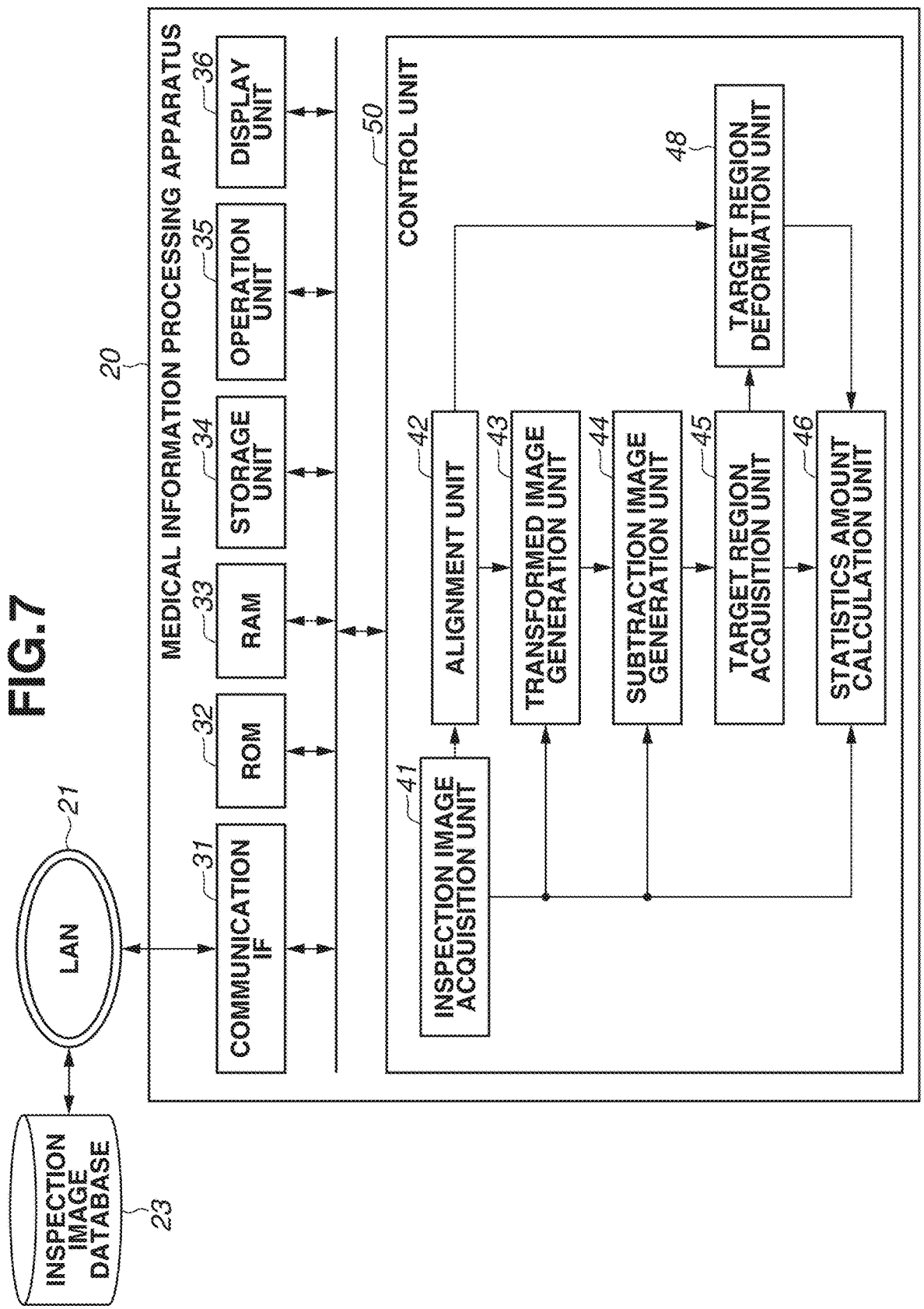
FIG. 7 is a block diagram illustrating an apparatus configuration of a medical information processing system according to a second exemplary embodiment.

FIG. 7 is a block diagram illustrating an overall configuration of a medical information processing system according to the second exemplary embodiment. Components common to the configuration of the medical information processing system according to the first exemplary embodiment are assigned the same reference numerals, and detailed descriptions thereof will be omitted. The medical information processing system includes the medical information processing apparatus 20 and the inspection image database 23 that are communicably connected with each other via a communication unit. While, in the present exemplary embodiment, the communication means is composed of a local area network (LAN) 21, it can be composed of a wide area network (WAN). The connection method of the communication means can be either wired connection or wireless connection.

The medical information processing apparatus 20 includes the communication IF 31, the ROM 32, the RAM 33, the storage unit 34, the operation unit 35, the display unit 36, and the control unit 50 as function components.

The control unit 50 is implemented by, for example, a CPU and integrally controls processing in the medical information processing apparatus 20. The control unit 50 includes the inspection image acquisition unit 41, the alignment unit 42, the transformed image generation unit 43, the subtraction image generation unit 44, the target region acquisition unit 45, the statistics amount calculation unit 46, and the target region transformation unit 48 as function components.

The target region transformation unit 48 transforms the target region acquired by the target region acquisition unit 45, based on the result of the alignment by the alignment unit 42.

At least a part of the units included in the control unit 50 can be implemented by an independent apparatus. In addition, each unit can be implemented by software for implementing each function. In this case, the software for implementing each function can operate on a cloud or server via a network. According to the present exemplary embodiment, each unit is assumed to be implemented by software in a local environment.

The configuration of the medical information processing system illustrated in FIG. 7 is to be considered illustrative. For example, the storage unit 34 of the medical information processing apparatus 20 can include the function of the inspection image database 23 and store a plurality of inspection images and additional information for a plurality of patients.

Overall processing of the medical information processing apparatus 20 according to the present exemplary embodiment will be described in detail below with reference to the flowchart illustrated in FIG. 8. While the following descriptions will be made centering on an example case where CT images are used as inspection images, the implementation of the present invention is not limited thereto. MRI images and ultrasonic wave images are also applicable.

In steps S2010 to S2030, the medical information processing apparatus 20 performs processing similar to the processing in steps S1010 to S1030, respectively, performed by the medical information processing apparatus 10 according to the first exemplary embodiment. Similar thereto, in steps S2040 to S2050, the medical information processing apparatus 20 performs processing similar to the processing performed in steps S1070 to S1080, respectively, according to the first exemplary embodiment. Detailed descriptions of the above-described processing will be omitted.

<Transforming Target Region>

In step S2060, the target region transformation unit 48 performs processing for transforming the target region R acquired in step S2040. Transformation in this processing refers to converting the target region R defined in the image coordinate system of the pre-treatment image I1 into the image coordinate system of the post-treatment image I2 and deriving the correspondence region R' in the post-treatment image I2. In other words, this processing is equivalent to an example of a correspondence region acquisition method for acquiring the correspondence region of the second image corresponding to the target region, based on the correspondence relation. More specifically, the statistics amount calculation unit 46 calculates the target region (i.e., correspondence region) R'(x) after the transformation, by performing the coordinate transformation on the target region R(x) through the calculation represented by the formula (7).

$$R'(x) = R\{D^{-1}(x)\} \quad (7)$$

A function $D^{-1}(x)$ is the inverse function of the transform function $D(x)$ acquired in step S2040. The function $D^{-1}(x)$ returns the image coordinate value of the position corresponding to the pre-treatment image I1 using an argument of the image coordinate value of the post-treatment image I2. Acquisition of the inverse function can be performed by using arbitrary known methods.

<Calculating Histogram of Post-Treatment Image>

In step S2070, the statistics amount calculation unit 46 performs processing for calculating the statistics amount for pixel values of the post-treatment image I2 included in the correspondence region R'. Specific processing is similar to the processing performed in step S2050 for generating a histogram of the pre-treatment image I1 in the target region R. The statistics amount calculation unit 46 performs processing for generating a histogram of the post-treatment image I2 in the correspondence region R'. In other words, this processing is equivalent to an example of a statistics amount calculation method for calculating the statistics amount for pixel values of the second image included in the correspondence region. The histogram H2 is calculated in this processing.

In step S2080, the medical information processing apparatus 20 performs processing similar to the processing in step S1095 performed by the medical information processing apparatus 10 according to the first exemplary embodiment. Detailed descriptions of the above-described processing will be omitted.

Processing of the medical information processing apparatus 20 according to the present exemplary embodiment is performed through the above-described method. This method has an effect of quantitatively measuring the statistics amount of pixel values in the target region in the pre-treatment image and the region in the post-treatment image corresponding to the target region (i.e., correspondence region). In particular, it is possible to set a measurement range after identifying the correspondence region between images based on the alignment between the images, and eliminate the influence of a local volume change occurring in the transformed image during measurement. This method provides an effect of achieving measurement with higher accuracy.

Other Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2018-025039, filed Feb. 15, 2018, which is hereby incorporated by reference herein in its entirety.

What is claimed is:

1. An information processing apparatus comprising:
an image acquisition unit configured to acquire a first image and a second image;
a correspondence relation acquisition unit configured to acquire a spatial correspondence relation between the first image and the second image;
an image transformation unit configured to acquire a transformed image by transforming the second image to a position corresponding to the first image based on the spatial correspondence relation;
a change calculation unit configured to calculate, at each position of the transformed image, a volume or area change between the transformed image and the second image based on the spatial correspondence relation; and
a statistics amount calculation unit configured to calculate a statistics amount for pixel values of the transformed image based on the volume or area change at each position.

2. The information processing apparatus according to claim 1, further comprising a target region acquisition unit configured to acquire a target region in the first image, wherein the statistics amount calculation unit calculates the statistics amount for pixel values of the transformed image corresponding to the target region based on the volume or area change.

3. The information processing apparatus according to claim 2, further comprising a subtraction image generation unit configured to generate a subtraction image between the first image and the transformed image, wherein the target region acquisition unit acquires a target region based on the subtraction image.

4. The information processing apparatus according to claim 1, wherein the statistics amount calculation unit corrects information about the pixel values of the transformed image based on the volume or area change and calculates the statistics amount.

5. The information processing apparatus according to claim 1, wherein the change calculation unit calculates, in a case where the first image and the second image are three-dimensional images, a volume change between the transformed image and the second image based on the spatial correspondence relation.

6. The information processing apparatus according to claim 1, wherein the change calculation unit calculates, in a case where the first image and the second image are two-dimensional images, an area change between the transformed image and the second image based on the spatial correspondence relation.

7. The information processing apparatus according to claim 1, further comprising a display control unit configured to display the transformed image or the second image and the statistics amount in an arranged manner on a display unit.

8. The information processing apparatus according to claim 7,
wherein the statistics amount is a second statistics amount,
wherein the statistics amount calculation unit further calculates a first statistics amount for pixel values of the first image, and
wherein the display control unit displays the transformed image or the second image and the second statistics amount in an arranged manner on the display unit and displays the first image and the first statistics amount in an arranged manner on the display unit.

9. The information processing apparatus according to claim 7, wherein the display control unit displays a histogram of the statistics amount on the display unit.

10. An information processing method, comprising:
acquiring a first image and a second image;
acquiring a spatial correspondence relation between the first image and the second image;
acquiring a transformed image by transforming the second image to a position corresponding to the first image based on the correspondence relation;
calculating, at each position of the transformed image, a volume or area change between the transformed image and the second image based on the spatial correspondence relation; and
calculating a statistics amount for pixel values of the transformed image based on the volume or area change at each position.

* * * * *